(12) United States Patent
Tauzin (10) Patent No.: US 9,782,490 B2
(45) Date of Patent: Oct. 10, 2017

(54) METHOD FOR CROSSLINKING HYALURONIC ACID; METHOD FOR PREPARING AN INJECTABLE HYDROGEL; HYDROGEL OBTAINED; USE OF THE OBTAINED HYDROGEL

(71) Applicant: ANTEIS S.A., Plan-les-Ouates (CH)

(72) Inventor: Bénédicte Vincente Tauzin, Bogeve (FR)

(73) Assignee: ANTEIS S.A., Plan-les-Ouates (CH)

( * ) Notice: Subject to any disclaimer, the term of this patent is extended or adjusted under 35 U.S.C. 154(b) by 13 days.

(21) Appl. No.: 14/896,504

(22) PCT Filed: Jun. 10, 2014

(86) PCT No.: PCT/EP2014/001573
§ 371 (c)(1),
(2) Date: Dec. 7, 2015

(87) PCT Pub. No.: WO2014/198406
PCT Pub. Date: Dec. 18, 2014

(65) Prior Publication Data
US 2016/0144043 A1    May 26, 2016

(30) Foreign Application Priority Data

Jun. 11, 2013 (FR) ..................................... 13 01332
Dec. 10, 2013 (WO) ................. PCT/FR2013/000328

(51) Int. Cl.
| | |
|---|---|
| A61K 31/167 | (2006.01) |
| A61K 47/48 | (2006.01) |
| A61K 8/02 | (2006.01) |
| A61K 9/00 | (2006.01) |
| C08B 37/08 | (2006.01) |
| A61L 27/20 | (2006.01) |
| A61K 8/73 | (2006.01) |
| A61Q 19/08 | (2006.01) |
| A61K 8/04 | (2006.01) |
| C08J 3/075 | (2006.01) |
| C08L 5/08 | (2006.01) |
| A61K 31/728 | (2006.01) |
| C08J 3/24 | (2006.01) |
| A61L 27/52 | (2006.01) |
| A61L 27/54 | (2006.01) |
| A61K 31/738 | (2006.01) |
| A61Q 19/00 | (2006.01) |

(52) U.S. Cl.
CPC ........ *A61K 47/4823* (2013.01); *A61K 8/0216* (2013.01); *A61K 8/042* (2013.01); *A61K 8/735* (2013.01); *A61K 9/0019* (2013.01); *A61K 31/167* (2013.01); *A61K 31/728* (2013.01); *A61K 31/738* (2013.01); *A61K 47/48784* (2013.01); *A61L 27/20* (2013.01); *A61L 27/52* (2013.01); *A61L 27/54* (2013.01); *A61Q 19/00* (2013.01); *A61Q 19/08* (2013.01); *C08B 37/0072* (2013.01); *C08J 3/075* (2013.01); *C08J 3/244* (2013.01); *C08J 3/247* (2013.01); *C08L 5/08* (2013.01); *A61K 2800/40* (2013.01); *A61K 2800/57* (2013.01); *A61K 2800/91* (2013.01); *A61K 2800/95* (2013.01); *A61L 2300/402* (2013.01); *A61L 2400/06* (2013.01); *A61L 2430/34* (2013.01); *C08J 2305/08* (2013.01)

(58) Field of Classification Search
None
See application file for complete search history.

(56) References Cited

U.S. PATENT DOCUMENTS

| | | | |
|---|---|---|---|
| 2010/0028435 A1 | 2/2010 | Gavard Molliard | |
| 2010/0303873 A1* | 12/2010 | Piron | A61K 8/042 424/401 |

FOREIGN PATENT DOCUMENTS

| | | |
|---|---|---|
| EP | 2011816 A1 | 1/2009 |
| WO | WO 96/33751 | 10/1996 |
| WO | WO 2005/085329 | 9/2005 |
| WO | WO 2009/071697 | 6/2009 |

OTHER PUBLICATIONS

International Search Report for PCT/EP2014/001573 dated Jul. 3, 2014.

* cited by examiner

*Primary Examiner* — Layla Berry
(74) *Attorney, Agent, or Firm* — Hueschen and Sage (57) ABSTRACT

The present invention relates to a method for crosslinking hyaluronic acid, a method for preparing an injectable hydrogel, the hydrogel thus obtained and its use.

19 Claims, 4 Drawing Sheets

METHOD FOR CROSSLINKING HYALURONIC ACID; METHOD FOR PREPARING AN INJECTABLE HYDROGEL; HYDROGEL OBTAINED; USE OF THE OBTAINED HYDROGEL

The object of the present invention is:
a method for crosslinking hyaluronic acid, or one of its salts, and optionally other biocompatible polymers,
a method for preparing an injectable hydrogel obtained according to said crosslinking method,
a hydrogel obtained according to said crosslinking method, and
the use of the hydrogel obtained according to said crosslinking method in the fields of aesthetics and medicine.

Hyaluronic acid is a polysaccharide formed by the repetition of a disaccharide unit consisting of D-glucuronic acid and N-actetylglucosamine. The structure is linear and without any species specificity. Hyaluronic acid is widely distributed in human and animal living organisms, in which it fulfills many biological functions such as for example the control of the hydration level or the maintaining of viscoelasticity of fluids or tissues. It is notably found in a high concentration in synovial liquid, the vitreous humor of the eye and in the dermis. A human being of 70 kilos has about 15 g of hyaluronic acid, half of which is contained in the skin and this amount decreases with ageing.

Hyaluronic acid gels are known and have been used in wide fields of aesthetics and medicine for many years. These gels are notably commonly injected:
  into the eyes, during ophthalmologic surgeries, in order to maintain the intra-ocular space and protect the tissues of the eye,
  into the joints, in the case of arthrosis, for supplementing the deficient synovial liquid and temporarily restoring the chondroprotective properties of said biological liquid,
  into or under the skin in order to fill wrinkles or increase the volume of certain areas of the face or of the body.

Hyaluronic acid has a short half-life in living organisms (less than 1 week). In the case of many applications in aesthetics and medicine, the administered injectable hydrogels contain hyaluronic acid stabilized by crosslinking, which gives the possibility of considerably increasing the lifetime (further called remanence) of this polysaccharide in vivo and therefore the duration of effectiveness of the injected product. Thus, by means of this modification by crosslinking, a hydrogel based on crosslinked hyaluronic acid has for example the capability of filling wrinkles over a period of several months.

In order to increase the remanence in vivo of an injectable hydrogel based on hyaluronic acid, one skilled in the art is aware that he/she may increase the degree of crosslinking of hyaluronic acid; but this modification of the molecule generates an increase in the viscosity of the gel and therefore difficulties in extruding it through a needle and subsequently in injecting this gel into the area desired by the practitioner. This necessarily implies:
  either limiting the crosslinking degree of hyaluronic acid and therefore the remanence of the gel in vivo, with the purpose of retaining a satisfactory ejection force,
  or using needles of larger diameter in order to be able to decrease the ejection force required for extruding the gel through this needle, which generates greater pain for the treated patient and also greater trauma (ecchymosis, red patch, inflammation, oedema, . . . ) at the injection area.

Many solutions have been proposed for overcoming this problem, workers seeking to provide injectable formulations having suitable remanence and viscosity properties and therefore satisfactory levels for extruding the gel through a needle. Mention may for example be made of:
  formulations based on particles of crosslinked hyaluronic acid obtained by disintegrating the crosslinked gel into particles, generally by grinding;
  various preparation methods have been described for obtaining this type of formulation, as is the case of application WO 97/04012,
  the formulations based on crosslinked hyaluronic acid containing different crosslinking identities from a specific preparation method described in application WO 2005/085329,
  formulations based on crosslinked hyaluronic acid containing mixtures of crosslinked gels which are not crosslinked with each other, i.e. not bound to each other through covalent bonds; these formulations are obtained according to a specific preparation method described in application FR 2 924 615, and
  formulations based on crosslinked hyaluronic acid, consisting of particles of crosslinked hyaluronic acid which are crosslinked together with a matrix of crosslinked hyaluronic acid; these formulations are prepared according to the application EP 2 011 816 or the application US 2010/0028435.

These solutions are however not fully satisfactory.

Application WO 97/04012 describes a specific manufacturing method giving the possibility of obtaining products based on polysaccharides (which may be hyaluronic acid) in the form of particles. Particulate gels based on crosslinked hyaluronic acid, also called "biphasic gels" in the literature, are characterized by the presence of particles with a diameter comprised between about 200 micrometers and more than 1,000 micrometers, dispersed in a solution of non-crosslinked hyaluronic acid which gives the possibility of facilitating ejection by a lubrication phenomenon. These gels are not totally satisfactory insofar that the extrusion of the gel through a needle is irregular, in particular with products which contain particles of large diameter; wherein the solution based on non-crosslinked hyaluronic acid playing the role of a carrier is rapidly resorbed in vivo, which involves an at least partial loss of the desired effect (notably a filling loss in the days following the injection for products which are dedicated to producing volume); and finally wherein the safety profile of the product is not so good (i.e. a greater level of secondary effects) than with a gel based on hyaluronic acid not containing any particles which may promote response to a foreign body and/or generate migration of these particles under the mechanical action of the treated area.

The application WO 2005/085329 describes a specific manufacturing method which is characterized by a step for initiating the crosslinking of a determined amount of at least one polymer (which may be hyaluronic acid), and then by adding an additional amount of polymer (which may be hyaluronic acid) with a molecular mass of more than 500,000 Da in solution with dilution of the reaction mixture so as to decrease the global concentration of the polymer in solution while continuing the crosslinking reaction. This solution does not give the possibility of having effective crosslinking of hyaluronic acid. Indeed, the addition of an additional amount of polymer is accompanied by dilution and therefore a decrease in the hyaluronic acid concentration of the reaction mixture. The probabilities of an encounter between the hyaluronic acid chains and the crosslinking agent are therefore reduced and the crosslinking reaction is not very effective.

Application FR 2 924 615 describes a manufacturing method characterized by the homogeneous mixture of x polymers (which may be hyaluronic acid), either identical or different, crosslinked prior to their mixing. By mixing is meant a juxtaposition of x polymers without generating covalent bonds between the latter. This solution is not completely satisfactory since the polymers are not bound to each other and therefore the thereby obtained gel may be dissociated within the injected area, notably under the action of mechanical stress which may be highly significant therein. For example mention may be made of the case of a product injected into the lips with the purpose of generating volume; the lips being subject to strong mechanical stresses. The experienced mechanical action may generate migration of the implanted gel and therefore secondary effects at the treated area but also around this area.

Application EP 2 011 816 relates to injectable gels of polysaccharides (which may be hyaluronic acid) comprising at least one first strongly crosslinked polysaccharide gel in the form of particles, and at least one weakly crosslinked polysaccharide gel forming a matrix; said at least one first gel being bound through covalent bonds to said at least one second gel. Unlike the products from application WO 97/04012, the strongly crosslinked particles are bound to the weakly crosslinked polysaccharide matrix; the migration of the particles is therefore strongly limited with this solution in the short and/or medium term but not in the long term (release of strongly crosslinked particles, with the possibility of migration, after the weakly crosslinked polysaccharide has been resorbed into the tissue). Since this solution comprises polysaccharide particles, which are strongly crosslinked, the risk of a response to a foreign body is therefore significant because of the particulate nature of the product and of the high degree of crosslinking of these particles (hyaluronic acid is therefore significantly modified, thus promoting non-recognition of the molecule by the organism).

The application US 2010/0028435 discloses a method for the preparation of formulations based on crosslinked hyaluronic acid, which are made of crosslinked hyaluronic acid particles that are co-crosslinked to a crosslinked hyaluronic acid matrix. Thus, the same comments as those given above for the application EP 2 011 816 apply mutatis mutandis.

The present invention gives the possibility of solving these different drawbacks by proposing a novel method for crosslinking hyaluronic acid, or one of its salts, or optionally other biocompatible polymers, the method giving the possibility of obtaining a hydrogel which is notably characterized by:

a good capability of being extruded through needles and therefore of being able to be injected easily by a practitioner in the area to be treated without this involving pains and significant trauma for the patient, no conversion of one or more constitutive phases of the hydrogel into particles during the crosslinking method (but exhibiting low injection forces despite the absence of particles that generally lower the injection force); the absence of co-crosslinked particles in the product leads to a significantly improved safety profile (fewer side effects and complications in the short and/or medium/long term), an enhanced capacity of integration/implantation of the hydrogel into the tissue (more even distribution of the product in the tissue), and also results in a significantly shorter and less complex production method (because the production does not involve tedious milling steps), remarkable viscoelastic properties arising from the specific structure of the obtained hydrogel, which provides the possibility of proposing to the practitioner a product having particular mechanical/rheological properties for meeting his/her expectations for treating the desired area, while observing its anatomy, the physiological mechanisms which govern it and, if applicable, the required mechanical/rheological properties which will allow it to correct the ascertained deficiency, a capability of being implanted in a simple way in tissues of the area to be treated because of the specific "multistructured" (and without co-crosslinked particles) structure of the obtained hydrogel, reinforced safety of the obtained hydrogel because of a better capability of not dissociating within the treated area and therefore not migrating towards other neighboring or more remote areas, notably under the action of mechanical stresses, a complex structure of the matrix of the obtained hydrogel, which is characterized as being "multistructured", thereby allowing optimization of the controlled release of active and/or biological substances when this is applicable, optimized remanence of the obtained hydrogel in order to extend the efficiency of the aesthetic or therapeutic treatment, thus giving the possibility of limiting the number of administrations per medical or surgical procedure For this purpose, the object of the invention is a novel method for crosslinking hyaluronic acid, or one of its salts, and optionally other biocompatible polymers, comprising at least the steps of:

a) preparing a first aqueous phase of hyaluronic acid, and optionally of other biocompatible polymers, partly crosslinked, characterized by:

adding hyaluronic acid or one of its salts and optionally other biocompatible polymers, into a aqueous solution in order to obtain a concentration C1 of hyaluronic acid, adding an amount Q1 of crosslinking agent, obtaining partial crosslinking of hyaluronic acid by controlling the temperature T1 and the duration t1 of the crosslinking reaction, wherein the prepared first aqueous phase of partially crosslinked hyaluronic acid is generally not converted into particles, b) preparing at least one second aqueous phase of hyaluronic acid, and optionally of other biocompatible polymers, partly crosslinked, characterized by:

adding hyaluronic acid or one of its salts and optionally other biocompatible polymers, into an aqueous solution in order to obtain a concentration C2 of hyaluronic acid, adding an amount Q2 of crosslinking agent, obtaining partial crosslinking of hyaluronic acid by controlling the temperature T2 and the duration t2 of the crosslinking reaction, wherein the prepared at least one second aqueous phase of partially crosslinked hyaluronic acid is generally not converted into particles, c) adding at least the second partly crosslinked hyaluronic acid phase into the first phase, and then performing mixing of said at least two phases by optionally adding an additional amount Qm of crosslinking agent, d) continuing the crosslinking of the mixture made beforehand by controlling the temperature Tm and the duration tm of the crosslinking reaction.

The crosslinking reaction of the mixture is then stopped, advantageously by dilution with an aqueous solution and/or by removal of the unreacted crosslinking agent by carrying out purification.

The crosslinking method according to the invention therefore consists of mixing during the crosslinking at least two aqueous phases of hyaluronic acid, and optionally of other biocompatible polymers, which have already partly crosslinked, and then continuing the crosslinking reaction in order to bind said at least two phases through covalent bonds.

By "partly crosslinked" is meant the fact that said at least 2 aqueous phases of hyaluronic acid, optionally containing other biocompatible polymers, still have available reaction sites at the polymeric chains which are able to react with a crosslinking agent for crosslinking/bridging new chains of hyaluronic acid and/or of other biocompatible polymers.

It is important to specify that the crosslinking method according to the invention does not involve the preparation and/or addition of crosslinked particles of hyaluronic acid, or of one of its salts, or of any other polymer, during the steps of said crosslinking method, i.e. during steps a, b, c and d as described above. All partially crosslinked phases are at no time converted into particles during said crosslinking method by, for example, grinding. The crosslinking method according to the invention therefore does not give the possibility of having crosslinked particles being crosslinked together with a gel of hyaluronic acid.

According to an embodiment of the invention, the second aqueous phase of partly crosslinked hyaluronic acid has a greater partial degree of crosslinking than that of the first aqueous phase of partly crosslinked hyaluronic acid. This particularity gives the possibility of facilitating the mixing of the second more strongly crosslinked phase within the first phase.

By "partial crosslinking degree" is meant the crosslinking level of the phase just before its mixing with another phase; the crosslinking level is only partial since it will further develop with the continuation of the crosslinking during the mixing of the phases. This crosslinking level may be determined for each relevant phase by experimentally measuring the degree of crosslinking and comparing it to the maximum theoretical degree of crosslinking (which may be calculated by evaluating the ratio of the number of moles of introduced crosslinking agent and of the number of moles of polymer units having the capability of crosslinking). The degree of crosslinking can be experimentally assessed either indirectly (e.g., by measurement of the ejection force, see example 2) or directly (e.g., by nuclear magnetic resonance spectrometry (NMR), for example using the method described by Kenne et al. (Kenne et al., Modification and cross-linking parameters in hyaluronic acid hydrogels—definitions and analytical methods, Carbohyr. Polym. 2013, 91:410-418).

Thus, in general, the "partial crosslinking degree" of the partially crosslinked phase is less than 90% (of the maximum of the theoretically calculated crosslinking degree), or less than 70%, or even less than 50%, or even less 30%, or even less than 10%.

According to an embodiment of the invention, the concentration $C_2$ of hyaluronic acid is greater than or equal to the concentration $C_1$. This particularity gives the possibility of facilitating the mixing of the more strongly concentrated second phase within the first phase but also obtaining greater swelling of the second phase within the first phase (hyaluronic acid having the capability of swelling in water, and all the more so since its concentration is significant). This then gives the possibility of promoting maximum steric "embedding" by entanglement of polymer chains of the second phase within the first but also promoting the crosslinking reaction which will bind the polymer chains of the first and of the second phases, because of greater physical proximity of these chains and therefore better efficiency of the reaction for bridging these chains.

According to an embodiment of the invention, the amount of crosslinking agent $Q_2$ is greater than or equal to the amount $Q_1$, in order to obtain a partial crosslinking degree greater for the second phase than for the first phase.

According to an embodiment of the invention, the crosslinking temperature $T_2$ is greater than or equal to the temperature $T_1$, in order to obtain a greater partial degree of crosslinking for the second phase than for the first. The crosslinking temperature Tm, itself, is greater than $T_2$ in order to maximize the efficiency of the crosslinking reaction allowing the first and second phases to be bound through covalent bonds.

According to an embodiment of the invention, the crosslinking duration $t_2$ is longer than or equal to the duration $t_1$, in order to obtain a greater partial degree of crosslinking for the second phase than for the first. The crosslinking duration tm, itself, may be longer than or equal to but also less than the durations $t_1$ and $t_2$. This duration tm depends on the selected temperature Tm for achieving crosslinking of the mixture of said at least two phases.

During the preparation of the mixture, the masses of the first and of the second phases may be equal or different. Depending on the properties which it is desired to give to the obtained hydrogel, according to the present invention, during the mixing, the presence of one phase shall appropriately be promoted relative to the other and therefore a larger mass of this phase should be used, with respect to the other. Thus, it may be stated that from a mechanical/rheological point of view, the phase which has the highest degree of crosslinking gives the gel according to the invention dominant elasticity and remanence properties with respect to the phase which has a lower degree of crosslinking. On the other hand, the phase which has the lowest degree of crosslinking gives a smaller ejection force to this phase and therefore easier use of the product to be injected. With the hydrogel according to the invention, synergy is therefore observed in the resulting properties in terms of mechanical/rheological, remanence and injectability characteristics. This synergy is obtained because of the optimization of the two parameters which act mutually on each other: the low degree of crosslinking of one of the phases promotes better injectability as well as cohesion and global flexibility of the hydrogel and reduces remanence and elasticity while the strong degree of crosslinking of the other phase promotes remanence, a further pronounced viscoelastic nature in favor of elasticity and a contrario reduces injectability, cohesion and flexibility. This synergy therefore gives the possibility of combining the advantages of each of the different constitutive phases by minimizing their drawbacks, while avoiding the drawbacks described beforehand with the compositions containing crosslinked polymer particles. The optimization of the proportions of each crosslinked phase within the hydrogel therefore gives the possibility of obtaining an easily injectable product with which it is possible to meet the different needs expressed for treatment in aesthetics or medicine in terms of injectability, mechanical/rheological properties and remanence.

According to an embodiment of the invention, the crosslinking of the mixture of the different partly crosslinked phases is stopped by achieving purification in order to remove the residual unreacted crosslinking agent. This purification is carried out according to techniques well-known to one skilled in the art such as for example with a dialysis bath or by washing with a continuous water flow. Preferably purification by dialysis is selected by using an iso-osmolar solution and having suitable pH. At the end of the crosslinking reaction of the mixture of the different partly crosslinked phases and before the gel purification step, it may be advantageous to neutralize the obtained gel, according to the standard methods known in the field, and for example by adding an acid when the crosslinking has been conducted in a basic medium, and by adding a base when the crosslinking has been conducted in an acid medium.

The invention deals with the crosslinking of hyaluronic acid or of one of its salts, and in particular its physiologically acceptable salts such as sodium, calcium, zinc, potassium salts, advantageously sodium salt. Hyaluronic acid may be of an animal origin or obtained by bacterial fermentation. It may have a molecular mass of a few Da to several million Da, advantageously about 0.1 to 4 million Da.

The invention also deals with the crosslinking of other biocompatible polymers, in combination with hyaluronic acid. These polymers of natural or synthetic origin should have chemical functions allowing them to crosslink and they should be biocompatible so as to be able to be put into contact with biological fluids or tissues. Mention may for example be made of the family of polysaccharides, polyesters, polyanhydrides, polyphosphazenes, poly-ε-caprolactone, polylactic acids and their derivatives, polyvinyl acids, polyacrylamides, N-vinyl pyrrolidone and acrylic polymers and biologically acceptable derivatives.

The crosslinking reactions are carried out in aqueous solutions in an acid or basic medium, advantageously in a basic medium having a pH preferably comprised between 8 and 13. The pH values of the solutions may be identical or different.

The crosslinking agents which are involved in the different crosslinking reactions may be identical or different. These are generally bi- or poly-functional crosslinking agents of different types and they may for example be selected from divinylsulfone, bi- or poly-functional epoxies, carbodiimides and formaldehydes. Preferably agents from the family of bi- or poly-functional epoxies are selected and notably 1,4-butanedioldiglycidylether (BDDE), diepoxy-octane or 1,2-bis-(2,3-epoxypropyl)-2,3-ethylene. The use of BDDE is most particularly preferred for each of the crosslinking reactions to be carried out.

The crosslinking temperatures are generally comprised between about 15° C. and 60° C. They are advantageously less than 35° C. for the crosslinking of partly crosslinked phases and greater than 45° C. for the crosslinking of the mixture of different partly crosslinked phases.

The crosslinking durations are generally of several hours, advantageously of more than 1 hour up to about 12 hours.

The crosslinking of the mixture of the different partly crosslinked phases is preferentially carried out with 2 phases, but it may also be carried out with more than 2 phases having different partial degrees of crosslinking.

The weight proportions of each partly crosslinked phase in the mixture to be crosslinked may strongly vary notably depending on the selected exact composition, on the partial degrees of crosslinking of the different relevant phases and on the final properties sought after. Generally, in the mixture, the weight proportion of the phase which has the highest partial degree of crosslinking is comprised between about 0.1 and 99.9%, or further between about 5 and 95%, or further between 10 and 90%, or further between 20 and 80%, or further between 30 and 70%, or further between 40 and 60%, or further between 45 and 55% of the total mass of the different phases of the mixture.

The crosslinking method according to the invention is different from those described in the prior art. None of these methods involves crosslinking consisting of mixing during the crosslinking at least 2 aqueous phases of hyaluronic acid and optionally of other biocompatible polymers, which have already been partly crosslinked, and then continuing the crosslinking reaction in order to bind said at least 2 phases through covalent bonds, without preparing and/or adding articles of crosslinked hyaluronic acid or a salt thereof, or of any other polymer, in the steps of said crosslinking method.

The relevant documents of the prior art considered as being the closest to the present invention are the following:

The application WO 97/04012 describes a specific crosslinking method for a polysaccharide which may be hyaluronic acid; a method comprising the steps:
putting the polysaccharide into an aqueous solution,
initiating the crosslinking reaction by adding a crosslinking agent,
introducing unfavorable steric conditions for the crosslinking reaction, these conditions being preferentially a dilution of the reaction mixture during the crosslinking, and
reintroducing favorable steric conditions for the crosslinking reaction, these conditions being preferentially a concentration of the reaction mixture by evaporation in order to complete the crosslinking reaction.

Unlike the present invention, this application does not involve the mixing of different partly crosslinked hyaluronic acid phases during the crosslinking.

On the other hand, the present invention is not characterized by providing unfavorable steric conditions (such as a dilution) and then favorable steric conditions (such as an evaporation) during the crosslinking reaction: the crosslinking according to the invention is carried out under favorable conditions in order to optimize the yield.

The application WO 2005/085329 describes a specific crosslinking method which is characterized by:
a step for initiating the crosslinking of a determined amount of at least one polymer, and
addition of an additional amount of polymer with a molecular mass of more than 500,000 Da in solution, with dilution of the reaction mixture so as to decrease the global concentration of the polymer in the solution while continuing the crosslinking reaction.

Unlike the present invention, this application does not involve the mixing of different partly crosslinked hyaluronic acid phases during the crosslinking.

This application involves an addition of polymer during the crosslinking reaction, but this polymer has not been subject to preliminary crosslinking, either partial or total. On the other hand, unlike the present invention, this polymer addition is necessarily accompanied by dilution of the reaction mixture having the consequence of providing unfavorable steric conditions and therefore not very efficient continuation of the crosslinking reaction.

Application FR 2 924 615 describes a method for preparing a hydrogel characterized by the homogeneous mixing of x polymers either identical or different, crosslinked prior to their mixing.

Unlike the present invention, this application does not involve the mixing of different partly crosslinked hyaluronic acid phases during the crosslinking.

The x polymers, crosslinked beforehand and the crosslinking reaction of which was stopped for each of them, are mixed in order to obtain simple juxtaposition of these x polymers without generating covalent bonds: there is no crosslinking between these different polymers.

The application EP 2 011 816 describes a method for preparing a hydrogel comprising the steps of:
  preparing particles of a first strongly crosslinked polysaccharide according to grinding techniques known to one skilled in the art in order to obtain particles with a desired grain size,
  suspending these particles,
  adding at least one second polysaccharide, and
  crosslinking said at least one second polysaccharide up to a crosslinking degree X2 for obtaining at least one second weakly crosslinked polysaccharide and crosslinking together said at least one weakly crosslinked second polysaccharide with said particles.

Unlike this application, the present invention does not involve the use of crosslinked particles (preparation and/or addition in the reaction mixture) during the crosslinking. Notably there is no grinding step allowing preparation of the crosslinked hyaluronic acid particles during the crosslinking method of the present invention:
  for partly crosslinked phases, before mixing these phases for continuing the crosslinking, and
  for mixing the partly crosslinked phases, during continuation of the crosslinking.

The application US 2010/0028435 describes a method for preparing an injectable gel similar to the one of the application EP 2 011 816.

The gel from the application US 2010/0028435 is obtained by achieving mutual crosslinking of crosslinked particles of hyaluronic acid with a gel of hyaluronic acid.

Unlike this application (but also unlike application EP 2 011 816), the crosslinking method according to the invention does not involve any preparation and/or addition of crosslinked particles of hyaluronic acid, or of one of its salts, or of any other polymer, during the steps of said crosslinking method. The crosslinking method according to the invention therefore does not allow mutual crosslinking of the crosslinked particles with a gel of hyaluronic acid.

The invention also relates to a method for preparing an injectable hydrogel formed by hyaluronic acid, or one of its salts, and optionally other biocompatible polymers, crosslinked according to the crosslinking method described earlier. This preparation method is characterized in that it comprises at least the following successive steps:
  crosslinking the hyaluronic acid, or one of its salts, and optionally other biocompatible polymers, according to the crosslinking method described earlier,
  purifying the mixture by means of an iso-osmolar solution having a suitable pH,
  homogenizing the mixture with optionally the addition of one or several other biocompatible polymers and/or of one or several substances which may provide a benefit to the organism like active substances,
  optional degassing and/or freeze drying,
  conditioning in a syringe or in a flask or in any other hermetic container, and
  sterilizing Advantageously, the injectable hydrogel according to the invention is conditioned in syringes, and then is sterilized according to any means known per se and preferentially by autoclaving, for direct use and/or marketing.

The invention also relates to a hydrogel obtained according to the crosslinking method described earlier. This hydrogel consists of at least crosslinked hyaluronic acid or one of its salts, and optionally of other biocompatible polymers, characterized by a mixture of several phases of crosslinked hyaluronic acid having different degrees of crosslinking, said phases being bound to each other through covalent bonds. The hydrogel obtained by the crosslinking method according to the invention can thus be characterized as being composed of a single "multistructured" crosslinked phase without co-crosslinked particles.

According to an aspect of the invention, the hydrogel may be based on a derivative of hyaluronic acid, i.e. based on the molecule obtained by modifying via a chemical route, or any other route, the hyaluronic acid molecule.

The hydrogel according to the invention has a good capability of being extruded through needles and therefore of being easily injected by a practitioner at the area to be treated without this involving pain and significant trauma for the patient. This advantage results from the "multistructured" complex matrix stemming from the crosslinking method according to the invention, which gives the possibility of promoting better injectability because of the lubrication induced by the presence within the product of a phase having a lower degree of crosslinking.

The hydrogel according to the invention does not include and is not composed of co-crosslinked particles. This offers the advantage of a significantly improved safety profile compared to particle-containing products (fewer side effects and complications in the short and/or medium/long term) and an enhanced capacity of integration/implantation of the hydrogel into the tissue (more even distribution of the product in the tissue).

Because of its "multistructured" feature, the hydrogel according to the invention has remarkable mechanical/rheological viscoelasticity properties (i.e. of viscosity and elasticity). The presence within the hydrogel according to the invention of at least 2 phases in equal or different proportions, and with different degrees of crosslinking, gives the possibility of optimally meeting the needs of practitioners for treating the desired area, while observing its anatomy, the physiological mechanisms which govern it and if applicable, the required mechanical/rheological properties which will allow it to correct the ascertained deficiency (for example, strong elasticity for generating volume around a cheekbone).

The hydrogel according to the invention has good capability of being "bio-implanted" in tissues. Its "multistructured" matrix provides great flexibility which allows optimized infiltration of the product into the tissues thereby allowing limitation of post-injection trauma and therefore limitation of side effects like pain at the injected area but also the inflammatory reaction following any injection.

The specific structure of the hydrogel, characterized by the fact that the different phases are bound to each other through covalent bonds, also allows reinforcement of the safety of the administered implant by improving the capability of the product of not dissociating and therefore of migrating towards other neighboring or more remote areas, notably under the action of mechanical stresses of the treated area.

The "multistructured" matrix of the hydrogel also gives the possibility of having phases with a high degree of crosslinking while preserving an injectable product, which induces better remanence of the hydrogel and therefore an extension of the efficiency of the aesthetic or therapeutic treatment, but further limiting the number of administrations per medical or surgical procedure.

The high safety level of the implant from the present invention, coupled with its specific complex structure notably giving it mechanical/rheological and bio-integration properties which may be adapted and optimized depending on the area to be treated, makes it a product of choice for controlled and/or delayed release of one or several substances which may provide a benefit to the organism and notably active substances and/or biological entities such as cells, enriched platelets, genes, DNA fragments or growth factors. The presence of different phases within the product, phases having different degrees of crosslinking but also different polymer concentrations, give the possibility of having release of each of these substances at different times and therefore optimizing the salting-out and action profile of one or several active ingredients or compounds of biological origin for local or general treatment.

The hydrogel according to the invention is advantageously implanted by injection into the tissues and/or fluids of living human or animal organisms.

The hydrogel according to the invention may also be used in a non-injectable form. In this case, the practitioner implants the sterile product from the present invention by depositing it at the area to be treated by means of suitable medical and/or surgical instruments.

The hydrogel according to the invention may also be used in compositions for topical use, according to a suitable formulation, for example on the skin, the hair, the nails, the cornea of the eye, the teeth, the lips, the internal or external mucosas and wounds. In this case, it may contain all the compounds which may provide one or several benefits to the area to be treated, such as for example vitamins, antioxidants, hydrating molecules, proteins, active substances either with a pharmacological action or not, biological entities such as cells, enriched platelets, genes, DNA fragments or growth factors, coloring agents, pigments, odorous molecules or aromatic molecules. These compounds are either dispersed in the hydrogel, or grafted to one or several of the polymers of the hydrogel, or contain/encapsulated in another material itself dispersed within the hydrogel.

According to an aspect of the invention, the total hydrogel concentration of hyaluronic acid, or of one of its salts, is comprised between 0.01 and 50 mg/ml, preferably between 1 and 35 mg/ml, advantageously between 8 and 30 mg/ml.

According to an aspect of the invention, the hydrogel according to the invention is partly or totally freeze-dried in order to obtain a semi-solid or a powder.

According to an aspect of the invention, the hydrogel according to the invention contains one or several active substances of natural or synthetic origin either with a pharmacological action or not, such as for example antioxidants, anti-inflammatories, antiseptics, antibacterial agents, antifungal agents, anticancer agents, local anesthetics, proteins, hormones, either alone or as a combination. These active substances are either dispersed in the hydrogel, or grafted to one or several polymers of the hydrogel, or contained/encapsulated in another material itself dispersed within the hydrogel. In the latter case, as an example, mention may be made of the encapsulation of an active substance, such as an anti-inflammatory, in microspheres based on a polymer derived from polylactic acid or poly-ϵ-caprolactone.

According to an aspect of the invention, the hydrogel according to the invention contains lidocaine dispersed within its crosslinked matrix.

According to an aspect of the invention, the hydrogel according to the invention contains one or several compounds of biological origin such as cells, enriched platelets, genes, DNA fragments or growth factors. These compounds are preferentially dispersed in the hydrogel, but they may also be grafted to one or several of the polymers of the hydrogel or contained/encapsulated in another material itself dispersed within the hydrogel.

According to an aspect of the invention, the hydrogel according to the invention contains polymers which are dispersed within the crosslinked matrix of the hydrogel. For example mention may be made of the polymers from the family of polysaccharides, polyesters, polyanhydrides, polyphosphazenes, poly-ϵ-caprolactone, polyactic acids and derivatives thereof, polyvinyl acids, polyacrylamides, N-vinyl pyrrolidone and acrylic polymers and biologically acceptable derivatives.

According to an aspect of the invention, the hydrogel according to the invention contains mineral substances which are dispersed within the crosslinked matrix of the hydrogel. For example mention may be made of hydroxyapatite or tricalcium phosphates like β tricalcium phosphate.

According to an aspect of the invention, the hydrogel according to the invention is mixed with one or several other substances, preferentially sterile, which may provide a benefit to the organism, just before its administration to a patient. The mixing is then carried out by the final user, i.e. by a practitioner or by authorized personnel, according to a suitable method using one or several mixing devices giving the possibility of producing a satisfactory mixture and of retaining sterility if required. For example, mention may be made of the mixing by the final user of the hydrogel according to the invention and of one or several compounds like active substances, biological entities or mineral substances:

- by performing round trips between two containers (one filled with the hydrogel according to the invention and the other filled with the compound to be dispersed in the hydrogel), these containers may for example be syringes, and
- by simultaneously extruding the contents of both containers (one filled with the hydrogel according to the invention and the other filled with the compound to be dispersed in the hydrogel) in order to bring together the different compounds and/or mix them in another container before administration to the patient.

The invention also relates to the use of the hydrogel obtained according to the crosslinking method described earlier for esthetic or therapeutic applications.

The benefits provided by the present invention make it possible to use the hydrogel obtained according to the crosslinking method described earlier for many applications in esthetics and medicine and notably for those already extensively described in the literature for hyaluronic acid (see, e.g., Volpi et al., Curr. Med. Chem. 2009, 16:1718-45).

The hydrogel according to the invention is therefore used for esthetic or therapeutic applications in humans or in animals. It is advantageously implanted in the organism of the patient by injection but it may also be implanted in non-injectable form and, in this case, it is deposited at the area to be treated by a practitioner by means of suitable medical and/or surgical instruments. Finally, it may be used by topical application.

The hydrogel according to the invention is notably used for:
- filling volumes,
- generating spaces within certain tissues, thereby promoting their optimal operation,
- replacing physiological liquids or deficient tissues,
- stimulating or promoting regeneration of the tissues,
- moisturizing and protecting tissues, and
- delivering substances which may provide a benefit to the organism and notably active substances and/or biological entities.

As an example, mention may be made of the uses of hydrogel in the following cases:
- formulating an intradermally or subcutaneously implantable composition for improving the quality of the skin, or filling wrinkles or restoring face volumes (cheekbones, chin, lips, nose, . . . ) or of the body,
- formulating a cosmetic or cosmeceutical having the purpose of moisturizing and/or providing compounds of different natures to the organism such as vitamins, antioxidants, hydrating molecules, active substance, biological entities, coloring agents, pigments, odorous molecules or aromatic molecules,
- formulating an ophthalmologic topical composition for example for hydrating the cornea over the long term,
- formulating a topical or implantable composition for dental use for example for filling parodontal pockets and/or for stimulating regeneration of the tissues around the tooth,
- formulating an intra-ocularly implantable composition, notably for application during surgery of the cataract, of the glaucoma, of presbyopia or of the vitreous,
- formulating intra-articularly implantable compositions for applications in orthopedia or in rheumatology notably within the scope of visco-supplementation of deficient synovial liquid for treating arthrosis but also bone reconstruction or regeneration of cartilage,
- formulating an urologically implantable composition for applications in the treatment of urinary or fecal incontinence,
- formulating a topical or implantable composition used in medicine or in general surgery within the scope of treating fibrosis or for improving the healing of wounds, and
- formulating a topical or implantable pharmaceutical composition allowing delayed and/or controlled release of active substances and/or biological entities for different medical applications.

EXAMPLES

The invention will now be illustrated in a non-limiting way by the following examples.

Sodium hyaluronate, sodium carboxymethylcellulose, lidocaine hydrochloride, phospho-calcium hydroxyapatite and the whole of the other compounds used in the examples have a high degree of purity.

The injectability of the prepared gels was determined by measuring the required force (in Newtons) for ejecting the gel contained in a glass syringe of 1 ml (BD Hypak SCF, 1 ml long RF-PRTC) through a given needle at a rate of 12.5 mm/min.

The rheological properties of the gels were measured at 25° C. by means of an AR2000 rheometer (TA Instruments) using a plane-plane geometry of 40 mm and a gap of 1000 μm.

Example 1

Preparation of a Gel 1 According to the Invention a) Preparation of a Partly Crosslinked Phase A 4.70 g of sodium hyaluronate (NaHA) fibers with a molecular mass of about equal to 3.0 MDa and having a humidity level of 13.8% were weighed, to which 45.75 g of an aqueous 1 wt. % NaOH solution were added.

The hydration of the fibers took 1 h 20 min, with regular manual homogenization with a spatula.

1.41 g of a solution of 1,4-butanediol diglycidylether (BDDE) diluted to 1:5 in a 1 wt. % NaOH solution were added to the reaction medium, followed by manual homogenization for 15 min.

The gel thus obtained was divided into three equal masses to prepare the following three fractions:
- Fraction 1 was introduced into a thermostatic bath at 30° C. for 1 h and was then diluted with a phosphate buffer solution containing HCl to obtain a concentration of NaHA of 20 mg/ml and a neutral pH (=phase A'). Phase A' was mechanically homogenized for 10 min (=gel A').
- Fraction 2 was introduced into a thermostatic bath at 50° C. for 2 h and was then diluted with a phosphate buffer solution containing HCl to obtain a concentration of NaHA of 20 mg/ml and a neutral pH (=phase A"). Phase A" was mechanically homogenized for 10 min (=gel A").
- Fraction 3 was introduced into a thermostatic bath at 30° C. for 1 h.

Let A be the obtained partly crosslinked phase.

b) Preparation of a Partly Crosslinked Phase B 5.25 g of sodium hyaluronate (NaHA) fibers with a molecular mass of about equal to 3.0 MDa and having a humidity level of 13.8% were weighed, to which 45.75 g of an aqueous 1 wt. % NaOH solution were added.

The hydration of the fibers took 1 h 20 min, with regular manual homogenization with a spatula.

2.73 g of a solution of 1,4-butanediol diglycidylether (BDDE) diluted to 1:5 in a in a 1 wt. % NaOH solution were added to the reaction mixture, followed by 15 min of manual homogenization with a spatula.

The gel thus obtained was divided into three equal masses to prepare the following three fractions:
- Fraction 1 was introduced into a thermostatic bath at 30° C. for 1 h and was then diluted with a phosphate buffer solution containing HCl to obtain a concentration of NaHA of 20 mg/ml and a neutral pH (=phase B'). Phase B' was mechanically homogenized for 10 min (=gel B').

Fraction 2 was introduced into a thermostatic bath at 50° C. for 2 h and was then diluted with a phosphate buffer solution containing HCl to obtain a concentration of NaHA of 20 mg/ml and a neutral pH (=phase B"). Phase B" was mechanically homogenized for 10 min (=gel B").

Fraction 3 was introduced into a thermostatic bath at 30° C. for 1 h.

Let B be the obtained partly crosslinked phase.

c) Combining the Partly Crosslinked Phases A and B and Continuing the Crosslinking 9.0 g of the partly crosslinked phase A were added into 13.0 g of the partly crosslinked phase B and subjected to mechanical mixing for 15 min at room temperature before immersion into a thermostatic bath at 50° C. for 2 h.

The crosslinked product was neutralized to pH=7.0 in a phosphate buffer solution containing HCl, in which it was allowed to swell for 24 h and then it was dialyzed for 24 h with a phosphate buffer solution in order to remove unreacted BDDE.

After mechanical homogenization for 10 min, a gel 1 having a sodium hyaluronate concentration of 20 mg/ml was obtained.

Example 2

Characterization of the Gel 1 of Example 1

The gels 1, A', A", B' and B" were introduced into glass syringes of 1 ml and the forces required for extruding the gels through a 27G½ needle at a rate of 12.5 mm/min are indicated in the table below.

| Tested gel | Ejection force (N) |
| --- | --- |
| 1 | 23.3 |
| A' | 6.1 |
| B' | 7.0 |
| A" | 6.7 |
| B" | 25.1 |

It is seen that:

the crosslinking reactions are partial for phases A and B. Indeed, the ejection forces of A" and B" are greater than that of A' and B', respectively, demonstrating that the gels A" and B" are more crosslinked than A' and B', and the gel 1 according to the invention has an ejection force lower than that of the B" and, thus, has a better injectability than the gel that has not been subjected to the crosslinking method according to the invention.

The rheological viscoelasticity properties G' and G" of gel 1 at 1.0 Hz are also measured.

| Tested gel | G' (1.0 Hz) in Pa | G" (1.0 Hz) in Pa |
| --- | --- | --- |
| 1 | 96 | 0.40 |

Example 3

Preparation of a Gel 2 According to the Invention a) Preparation of a Partly Crosslinked Phase C 4.2 g of sodium hyaluronate (NaHA) powder with a molecular mass of about equal to 2.0 MDa and having a humidity level of 6.3% were weighed, to which 0.3 g of sodium carboxymethylcellulose (42 mPa·s, 2% in water, at 20° C.) with a humidity level of 2.0%, and 33.6 g of an aqueous 1 wt. % NaOH solution were added.

The hydration of the powder took 1 h 20 min, with regular manual homogenization with a spatula.

Let H be the obtained hydrated phase.

1.80 g of a 1,4-butanediol diglycidylether (BDDE) solution diluted to 1:5 in a 1 wt. % NaOH solution were added to 27.0 g of phase H, then a manual homogenization with a spatula was carried out for 15 min, followed by introducing the reaction mixture into a thermostatic bath at 50° C. for 1 h 30 min.

b) Preparation of a Partly Crosslinked Phase D 0.10 g of a 1,4-butanediol diglycidylether (BDDE) solution diluted to 1:5 in a 1 wt. % NaOH solution were added to 3.0 g of phase H obtained above, then a manual homogenization with a spatula was carried out for 15 min, followed by introducing the reaction mixture into a thermostatic bath at 50° C. for 2 h.

c) Combining the Partly Crosslinked Phases C and D and Continuing the Crosslinking The partly crosslinked phase D was added to the partly crosslinked phase C and was subjected to mechanical mixing for 15 min at room temperature before immersion into a thermostatic bath at 50° C. for 2 h 30 min.

The crosslinked product was neutralized to pH=7.0 in a phosphate buffer solution containing HCl, in which it was allowed to swell for 24 h and then it was dialyzed for 24 h with a phosphate buffer solution in order to remove unreacted BDDE.

After mechanical homogenization for 10 min, a gel 2 having a sodium hyaluronate concentration of 20 mg/ml was obtained.

Example 4

Preparation of an Injectable Formulation 1 According to the Invention

In 25% of the mass of gel 2 obtained in Example 3, 0.3 wt. % of lidocaine hydrochloride powder was added and mechanical homogenization was carried out for 15 min.

The thus obtained gel was introduced into 1 ml glass syringes, and then the syringes were sterilized in an autoclave at 121° C. for 20 min.

Example 5

Preparation of an Injectable Formulation 2 According to the Invention

In 25% of the gel mass 2 obtained in Example 3, 30 wt. % of a phospho-calcium hydroxyapatite powder with a particle size of between 30 and 50 μm was added and mechanical homogenization was carried out for 15 min.

The thus obtained gel was introduced into 1 ml glass syringes, and these syringes were then sterilized in an autoclave at 121° C. for 20 min.

Example 6

Characterization of the Injectable Formulation 1 of Example 4

The sterile formulation obtained in Example 4 was found to be easily injectable through a thin 27G½ needle; an injection force of 21.3 N was measured at a rate of 12.5 mm/min.

The pH and the osmolarity of this formulation are physiological:
pH=6.9
Osmolarity=290 mOsm/kg $H_2O$ The rheological characterizations resulted in an elastic modulus G' of 74 Pa and a Tan δ of 0.25 at a frequency of 1.0 Hz.

It is important to note that these rheological characteristics are compatible with injection into the dermis or subcutaneously.

In two 10 ml flasks F1 and F2 containing 8 ml of purified water, were introduced:
- 1 ml of Restylane® (Galderma Q-Med, Uppsala, Sweden) gel into F1; Restylane® is a product based on crosslinked hyaluronic acid at 20 mg/ml known for more than 10 years in esthetic medicine, and
- 1 ml of the injectable formulation 1 into F2.

F1 and F2 were manually stirred for 5 seconds. After a further 10 seconds, it was seen that the Restylane® product is completely dissociated in water (suspension of crosslinked hyaluronic particles in water), which is not the case for the injectable formulation 1 which was always in the form of a gel in water. The cohesivity level of the injectable formulation 1 is therefore much higher than that of the Restylane® product.

Example 7

Comparison of the Production of a Gel According to the Invention with the Prior Art (US 2010/0028435)

a) Preparation of a Gel 2 According to the Invention
See Example 3.

b) Preparation of a Prior Art Gel X According to Example 4 of US Application 2010/0028435

3.50 g of sodium hyaluronate (NaHA) powder with a molecular mass of about equal to 2.0 MDa and having a humidity level of 6.3% were weighed, to which 24.0 g of an aqueous 1 wt. % NaOH solution were added.

The hydration of the powder took 1 h, followed by manual homogenization for 10 min with a spatula.

700 μl of BDDE were added to the reaction medium, followed by manual homogenization for 10 min with a spatula before immersion into a thermostatic bath at 50° C. for 2 h.

The crosslinked product was neutralized to pH=7.0 in a phosphate buffer solution containing HCl, in which it was allowed to swell for 24 h (end volume=92 ml).

The gel thus obtained was grinded into particles by serial passage of the same through a grid of 250 μm.

Let Xp be the obtained particles.

3.50 g of sodium hyaluronate (NaHA) powder with a molecular mass of about equal to 2.0 MDa and having a humidity level of 6.3% were weighed, to which 30.5 g of an aqueous 1 wt. % NaOH solution were added.

The hydration of the powder took 1 h followed by a manual homogenization of 10 min with a spatula.

263 μl of BDDE were added to the reaction medium, followed by a manual homogenization for 10 min with a spatula before immersion into a thermostatic bath at 50° C. for 2 h.

Let Xg be the obtained crosslinked product.

58 g of particles Xp and 24 g of an aqueous 1 wt. % NaOH solution were added to the crosslinked product Xg, followed by homogenization with a spatula for 10 min and continuation of the crosslinking reaction for 6 h at 25° C.

The crosslinked product was neutralized to pH=7.0 in a phosphate buffer solution containing HCl, in which it was allowed to swell for 24 h, and then it was dialyzed for 24 h with a phosphate buffer solution in order to remove unreacted BDDE.

After mechanical homogenization for 30 min, a gel X was obtained.

c) Comparison of the Production Processes of Gel 2 and Gel X

The gel 2 and the gel Y were filled into glass syringes of 1 ml and extruded through needles of 27G½ (6 tests for each gel/manual injection by an operator). The gel 2 and the gel X were easily injectable through the needle, however, it is important to note that the gel 2 according to the invention was found to have a much better homogeneity within the syringe. In fact, during the injections, the operator carrying out the test observed many irregularities with the X gel (not the case with gel 2 of the invention) with regard to the force that must be applied to the syringe plunger; irregularities characterized by the operator as "pushs". On the other hand, among the six syringes tested for gel X, two syringes could not be completely discharged because the needle was completely blocked/obstructed by the gel (not the case with gel 2 according to the invention).

As described above, the prior art teaches that the conversion of a crosslinked gel into particles enables to decrease the ejection force of the product and, thus, to enhance its injectability through a needle (the strongly crosslinked hydrogel is grinded into particles of small size that are more likely to pass through the needle hole). Surprisingly, the gel 2 of the invention, which was not subjected to any grinding step of partially crosslinked phases (one of which is highly crosslinked and the other being less crosslinked), but has a crosslinked phase obtained from combining and crosslinking of the said two partly crosslinked phases, was also found to be readily injectable and also more homogeneous. The complex "multistructured" (and without co-crosslinked) structure according to the invention makes it therefore possible to address the problem of injectability described in the prior art without having to grind the product to convert it into particles.

Toluidine blue staining tests were performed on gel samples taken during the process of preparing gel 2 and gel X in order to evaluate if the structure of the gel is particulate or not. For this purpose, about 0.1 g of gel to be tested were disposed on a glass slide and five drops of an aqueous solution of toluidine blue (0.1 g toluidine blue per 100 g of deionized water) were added, and then a second glass slide was placed on the first glass slide. The result was then viewed under a microscope at a magnification of 40× and a picture was taken.

The following color tests were performed:
For gel 2: for the partly crosslinked phases C and D (see FIGS. 1 and 2) and for the crosslinked product obtained from the partly crosslinked phases C and D (see FIG. 3), after neutralization to a neutral pH for three samples;

For gel X: for the particles Xp (see FIG. 4) and for the crosslinked product obtained by co-crosslinking of particles Xp (see FIG. 5), after neutralization to a neutral pH for two samples.

Figure 1:
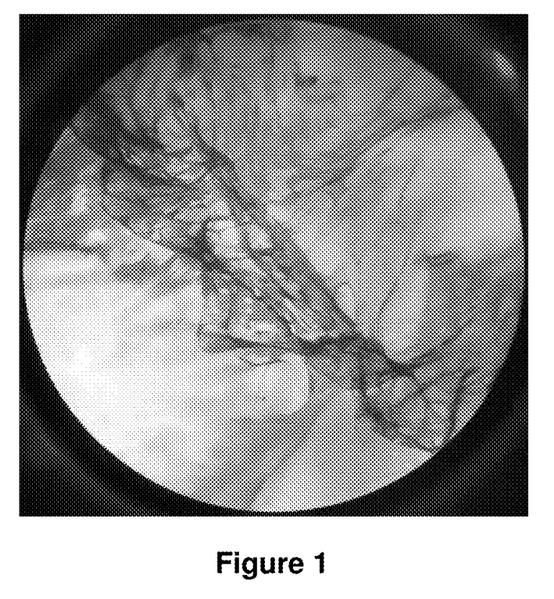
FIG. 1. For gel 2: the partly crosslinked phases C and D.
Figure 2:
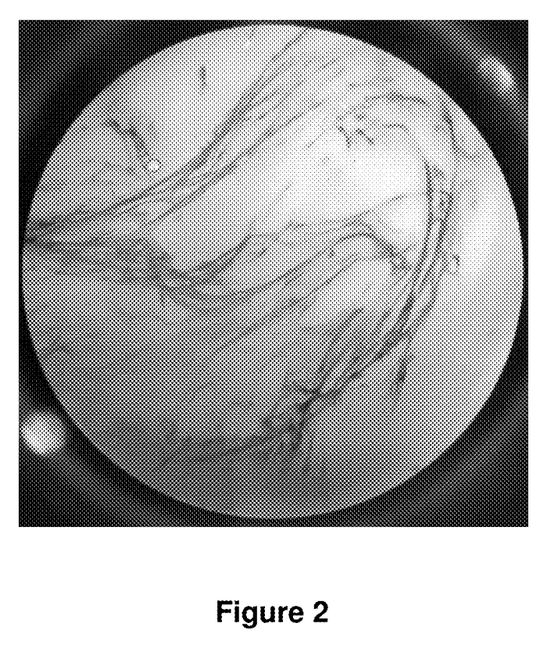
FIG. 2. For gel 2: the partly crosslinked phases C and D.
Figure 3:
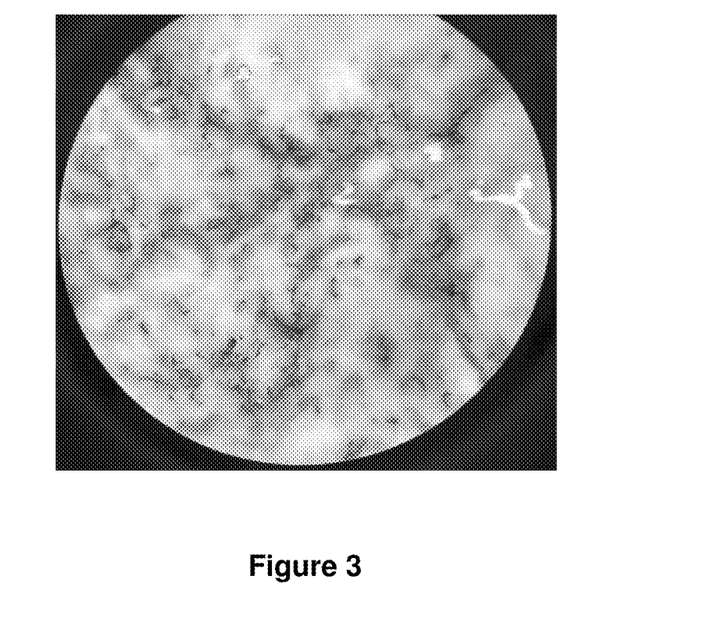
FIG. 3. For gel 2: the crosslinked product obtained from the partly crosslinked phases C and D.
Figure 4:
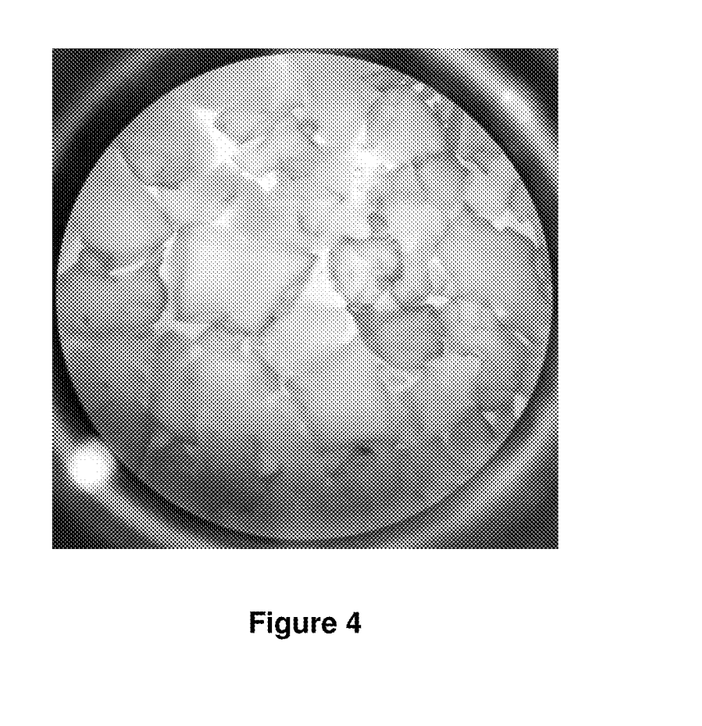
FIG. 4. For gel X: the particles Xp.
Figure 5:
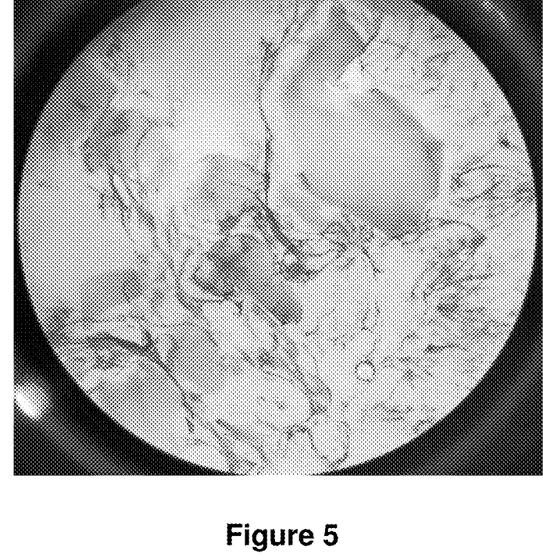
FIG. 5. For gel X: the crosslinked product obtained by co-crosslinking of particles Xp.

In contrast to FIG. 4 (and also FIG. 5), in which NaHA crosslinked particles are clearly visible, the gel structure of FIGS. 1 to 3 relating to gel 2 according to the invention is not particulate. The non-conversion of the partly crosslinked phases during the crosslinking method of the invention allows one to obtain a hydrogel which does not contain particles of co-crosslinked NaHA.

This represents a significant advantage over the prior art products, and especially over the products described in US 2010/0028435 and also in EP 2 011 816. Indeed, as described in the literature and also in the applications US 2010/0028435 and EP 2 011 816, the crosslinked particles generate side effects and complications in the short term as well as in the long term (in EP 2 011 816, crosslinked particles are specifically described as generating more or less strong reactions against foreign matters). In the present invention, the absence of co-crosslinked particles thus represents a major improvement over the inventions disclosed in US 2010/0028435 and EP 2 011 816 with respect to a better safety profile of the product while remaining easily injectable.

On the other hand, it is also important to note that US 2010/0028435 and EP 2 011 816 claim to limit migration of highly crosslinked particles within the body due to the co-crosslinking of these particles with a weakly crosslinked NaHA matrix. This is true in the short term, but the migration of highly crosslinked particles becomes possible again in the longer term, when the matrix of cross-linked weakly crosslinked NaHA has been resorbed. This latter point further corroborates the improved safety profile of the injectable hydrogel according to the invention, where the problem of migration of co-crosslinked particles in the long term does not arise (the hydrogel according to the invention does not contain co-crosslinked particles).

Another major advantage is the better integration (=bio-integration/bio-implantation) into tissues of the product according to the invention compared with the products of co-crosslinked particles known from US 2010/0028435 and also from EP 2 011 816. Indeed, as described in various scientific publications (e.g., Tran C. et al., In vivo bio-integration of three HA fillers in human skin: a histological study, Dermatology 2014, 228:4754; or Micheels, P. et al., Superficial dermal injection of HA soft tissue fillers: comparative ultrasound study, Dermatol. Surg. 2012, 38:1162-1169), the injection of products based on particulate, cross-linked NaHA into the dermis (e.g., of the products disclosed in US 2010/0028435 and EP 2 011 816) are distributed significantly more heterogeneous as compared to products based on non-particulate, crosslinked NaHA (as in case of the hydrogel according to the invention).

It is also important to note that the method of preparing a hydrogel according to the invention requires a significantly shorter time for manufacturing a product compared to the methods described in US 2010/0028435 and EP 2 011 816. A comparison of the manufacturing time for the gel 2 of the invention (approximately 55 h) and gel X according to US 2010/0028435 (approximately 85 h) may illustrates this point. This provides a clear economic advantage and also minimizes the risk of bacterial contamination of the gel during manufacturing, which increases with duration of the manufacturing process.

Example 8

Comparison of the Production of a Gel According to the Invention with the Prior Art (EP 2 011 816)

a) Preparation of a Gel 2 According to the Invention
See Example 3.

b) Preparation of a Prior Art Gel Y According to Example 1 of EP Application 2 011 816

1.00 g of sodium hyaluronate (NaHA) powder with a molecular mass of about equal to 2.0 MDa and having a humidity level of 6.3% were weighed, to which 6.2 g of an aqueous 1 wt. % NaOH solution were added.

The hydration of the powder took 1 h 20 min, with regular manual homogenization with a spatula.

0.15 g of BDDE were added to the reaction medium, followed by manual homogenization for 10 min with a spatula before immersion into a thermostatic bath at 50° C. for 2 h 30 min.

The crosslinked product was introduced into deionized water for 24 h, wherein three successive baths, each for 8 h, were used, in order to remove unreacted BDDE.

The gel thus obtained was grinded into particles by serial passage of the same through a grid of 250 μm and the particles were left to drain for 2 h.

Let Yp be the obtained particles.

5.0 g of particles Yp were added to 0.8 g of sodium hyaluronate (NaHA) powder with a molecular mass of about equal to 2.0 MDa and having a humidity level of 6.3%, to which 2.0 g of an aqueous 1 wt. % NaOH solution were added.

The mixture was manually homogenized for 30 min before addition of 0.03 g BDDE and then again homogenized for 30 min before immersion of the reaction mixture into a thermostatic bath at 50° C. for 2 h 30 min.

Let Yg be the obtained crosslinked product.

The crosslinked product Yg was neutralized to pH=7.0 in a phosphate buffer solution containing HCl, in which it was allowed to swell for 24 h, and then it was dialyzed for 24 h with a phosphate buffer solution in order to remove unreacted BDDE.

After manual homogenization for 30 min, a gel Y was obtained.

c) Comparison of the Production Processes of Gel 2 and Gel Y

As in Example 7, the gels 2 and Y were filled into glass syringes of 1 ml and extruded through a needle of 27G½. It was found that the two gels were easily injectable through the needle and the same comments as those set out in relation to Example 7 apply: the gel 2 according to the invention was found to be more homogeneous since its injection through the needle was more regular as that of gel Y. Surprisingly, although the gel 2 of the invention, which was not subjected to any grinding step into particles in order to facilitate its injectability, the complex "multistructured" structure of gel 2 exhibits a low ejection force similar to that of gel Y, which was subjected to a step of converting its strongly crosslinked phase into particles.

As in Example 7, toluidine blue staining was performed on gel samples taken during the process of preparing gel 2 and gel Y.

Figure 6:
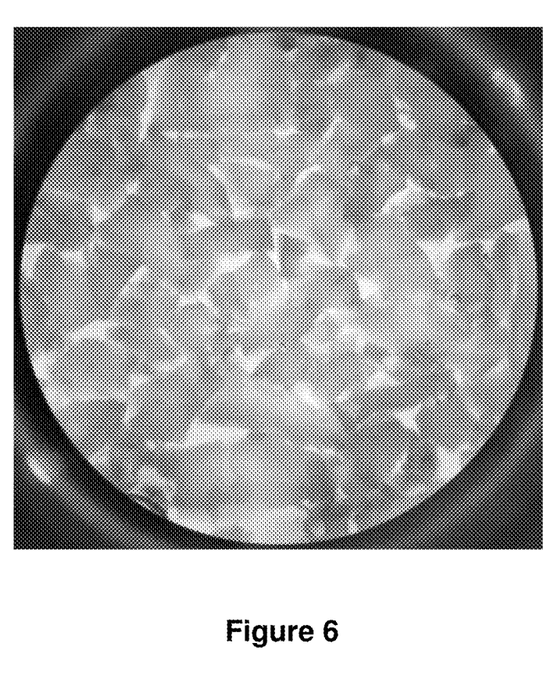
FIG. 6. For gel Y: the particles Yp.
Figure 7:
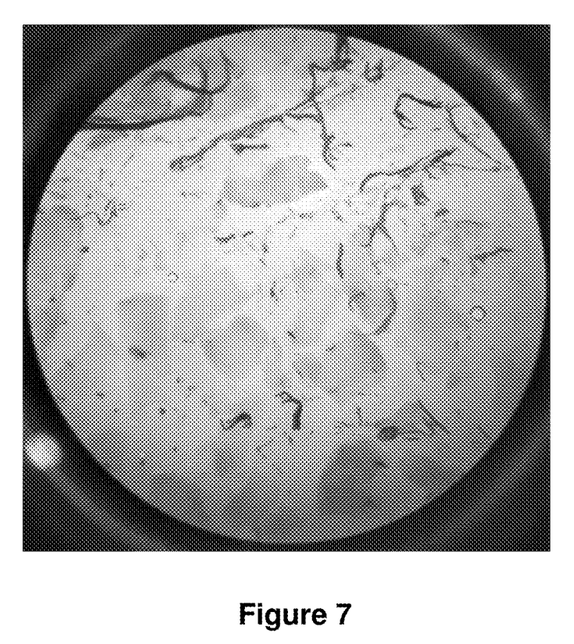
FIG. 7. For gel Y: the crosslinked product obtained by co-crosslinking of particles Yp.

The following color tests were performed:
For gel 2: for the partly crosslinked phases C and D (see FIGS. 1 and 2) and for the crosslinked product obtained from the partly crosslinked phases C and D (see FIG. 3), after neutralization to a neutral pH for three samples;

For gel Y: for the particles Yp (see FIG. 6) and for the crosslinked product obtained by co-crosslinking of particles Yp (see FIG. 7), after neutralization to a neutral pH for two samples.

The conclusion is the same as that of Example 7. In contrast to FIG. 6 (and also FIG. 7), in which NaHA crosslinked particles are clearly visible, the gel structure of FIGS. 1 to 3 relating to gel 2 according to the invention is not particulate.

Therefore, the present invention allows one to obtain an easily injectable hydrogel, despite the fact that it was not grinded (partly or entirely) to form particles during its crosslinking process. Thus, the absence of co-crosslinked particles in the gel enables to achieve a significant improvement (compared to the gel obtained in EP 2 011 816):

- the safety profile in the short and long term is improved, in particular there is no migration of highly crosslinked particles in the long term as in EP 2 011 816;
- the bio-integration of the gel into tissues is enhanced (more homogeneous distribution) due to the absence of co-crosslinked particles.

Finally, as in Example 7, it is important to note that the manufacture of the gel according to the invention has an economic advantage and minimizes the risk of particulate and bacterial contamination since the manufacturing process is significantly faster than that described in EP 2 011 816 (approximately 55 h for the gel according to the invention as compared to 83 h for the gel according to EP 2 011 816), and it does not require one or several complex and tedious milling steps as those required in EP 2 011 816.

The invention claimed is:

1. A method for crosslinking hyaluronic acid, or one of its salts, comprising at least the steps of:
   a) preparing a first aqueous phase of partly crosslinked hyaluronic acid comprising:
      i) adding hyaluronic acid, or one of its salts, in an aqueous solution to obtain a hyaluronic acid concentration $C_1$,
      ii) adding an amount $Q_1$ of crosslinking agent, and
      iii) achieving partial crosslinking of the hyaluronic acid by controlling the temperature $T_1$ and the duration $t_1$ of the crosslinking reaction,
   wherein the prepared first aqueous phase of partially crosslinked hyaluronic acid is not converted into particles;
   b) preparing at least one second aqueous phase of partly crosslinked hyaluronic acid comprising:
      i) adding hyaluronic acid, or one of its salts, in an aqueous solution to obtain a hyaluronic acid concentration $C_2$,
      ii) adding an amount $Q_2$ of crosslinking agent, and
      iii) achieving partial crosslinking of the hyaluronic acid by controlling the temperature $T_2$ and the duration $t_2$ of the crosslinking reaction,
   wherein the prepared at least one second aqueous phase of partially crosslinked hyaluronic acid is not converted into particles;
   c) adding the at least one second partly crosslinked hyaluronic acid phase into the first aqueous phase, and then producing a mixture of the at least two phases by optionally adding an additional amount $Q_m$ of crosslinking agent; and
   d) continuing the crosslinking of the mixture by controlling the crosslinking temperature $T_m$ and the duration $t_m$ of the crosslinking reaction,
   wherein the crosslinking during steps a), b), c) and d) does not involve the addition of crosslinked hyaluronic acid particles or one of its salts.

2. The method of claim 1, wherein the second aqueous phase of partly crosslinked hyaluronic acid has a partial degree of crosslinking greater than that of the first aqueous phase of partly crosslinked hyaluronic acid and/or in that the hyaluronic acid concentration $C_2$ is greater than or equal to the concentration $C_1$.

3. The method of claim 1, wherein the amount of crosslinking agent $Q_2$ is greater than or equal to the amount $Q_1$ and/or in that the crosslinking temperature $T_2$ is greater than or equal to the temperature $T_1$.

4. The method of claim 1, wherein the crosslinking duration $t_2$ is greater than or equal to the duration $t_1$ and/or in that the respective masses of the first and of the second partly crosslinked hyaluronic acid aqueous phases in the mixture are different.

5. The method of claim 1, wherein the crosslinking of the mixture is stopped by dilution with an aqueous solution and/or by removing the unreacted crosslinking agent by carrying out purification achieved by dialysis.

6. The method of claim 1, wherein the crosslinking reactions are carried out by the action of one or more polyfunctional crosslinking agents selected from the group consisting of bi-functional epoxies, poly-functional epoxies, divinylsulfone, carbodiimides and formaldehyde.

7. The method of claim 6, wherein the crosslinking agent is 1,4-butanedioldiglycidylether (BDDE).

8. The method of claim 1, wherein the salts of hyaluronic acid are selected from the group consisting of sodium, calcium, zinc and potassium.

9. The method of claim 1, wherein the hyaluronic acid, or one of its salts, in step a), or in step b), or in steps a) and b) exhibits a molecular mass of between 0.1 and 4 million Daltons.

10. The method of claim 1, wherein the hyaluronic acid, or one of its salts, in step a), or in step b), or in steps a) and b) is a derivative of hyaluronic acid obtained by modifying the hyaluronic acid via a chemical route, or via any other route.

11. A method for preparing an injectable hydrogel, comprising at least the following successive steps:
   a) crosslinking of hyaluronic acid, or of one of its salts, according to claim 1,
   b) purifying the crosslinked hyaluronic acid by means of an iso-osmolar solution and having a suitable pH,
   c) homogenizing the crosslinked hyaluronic acid, and optionally adding one or more other biocompatible polymers and/or one or more active substances,
   d) optionally degassing and/or freeze drying,
   e) conditioning in a syringe, in a flask, or in any other hermetic container, and
   f) sterilizing.

12. A hydrogel obtained according to the method of claim 11, comprising at least crosslinked hyaluronic acid or one of its salts, wherein the crosslinked hyaluronic acid is in a mixture of at least two crosslinked hyaluronic acid phases having different degrees of crosslinking, the phases being bound to each other through covalent bonds, wherein the total concentration of hyaluronic acid or of one of its salts is comprised between 0.01 and 50 mg/ml.

13. The hydrogel of claim 12, further comprising one or more active substances, having pharmacological action or not, selected from the group consisting of antioxidants, anti-inflammatories, antiseptics, antibacterial agents, antifungal agents, anticancer agents, proteins, hormones, local anesthetics, biological entities, and combinations thereof.

14. The hydrogel of claim 12, comprising lidocaine and/or one or more mineral substances.

15. A kit comprising the hydrogel of claim 12, wherein the hydrogel has been conditioned in sterile syringes.

16. The hydrogel of claim 12 for use in esthetic or therapeutic applications or for formulating an intradermally or subcutaneously implantable composition for improving the quality of the skin or filling the wrinkles or restoring volumes of the face or of the body, for the formulation of a cosmetic or cosmeceutical composition, for the formulation of a topical or intra-ocular composition, for applications in ophthalmology, for the formulation of a topical or implantable composition for applications in dentistry, for the formulation of an intra-articular composition for applications in orthopedia and rheumatology, for the formulation of an implantable composition in urology, for applications in the treatment of incontinence, for the formulation of a topical or implantable composition used in medicine or general surgery within the scope of treating fibrosis or for improving healing of wounds, for the formulation of a topical or implantable pharmaceutical composition allowing delayed and/or controlled release of active substances for various medical applications.

17. The method of claim 1, wherein steps a) i) and/or b) i) comprise adding other biocompatible polymers, and wherein the crosslinking during steps a), b), c) and d) does not involve the addition of crosslinked biocompatible polymers.

18. The method of claim 1, wherein the crosslinking temperature Tm is greater than the temperature T2.

19. The method of claim 1, wherein the crosslinking duration t2 is greater than or equal to the duration t1 and/or in that the respective masses of the first and of the second partly crosslinked hyaluronic acid aqueous phases in the mixture are equal.

* * * * *